United States Patent
Barker (10) Patent No.: US 7,025,205 B2
(45) Date of Patent: Apr. 11, 2006

(54) METHOD AND PACKAGING FOR PRESSURIZED CONTAINERS

(75) Inventor: Frank C. Barker, West Malling (GB)

(73) Assignee: Aventis Pharma Limited, West Malling (GB)

( * ) Notice: Subject to any disclaimer, the term of this patent is extended or adjusted under 35 U.S.C. 154(b) by 250 days.

(21) Appl. No.: 10/603,214

(22) Filed: Jun. 25, 2003

(65) Prior Publication Data
US 2004/0168950 A1 Sep. 2, 2004

Related U.S. Application Data

(60) Provisional application No. 60/394,421, filed on Jul. 8, 2002.

(30) Foreign Application Priority Data

Jun. 26, 2002 (GB) .................................... 0214667

(51) Int. Cl.
B65D 81/26 (2006.01)
(52) U.S. Cl. ....................................... 206/438; 206/205
(58) Field of Classification Search ................. 53/400, 53/428, 449, 459, 461, 463; 206/204, 205, 206/207, 210, 213.1, 363–370, 438, 484, 206/439, 484.1, 570–572, 0.6, 0.7; 383/109, 383/113; 604/840.1
See application file for complete search history.

(56) References Cited

U.S. PATENT DOCUMENTS

| 3,442,686 A | 5/1969 | Jones |
| 4,145,001 A | 3/1979 | Weyenberg et al. |
| 4,150,744 A | 4/1979 | Fennimore |
| 4,332,845 A | 6/1982 | Nawata et al. |
| 4,407,897 A | 10/1983 | Farrell et al. |
| 4,449,632 A | 5/1984 | Marusiak, Jr. |
| 4,528,234 A | 7/1985 | Kaiho et al. |
| 4,657,133 A | 4/1987 | Komatsu et al. |
| 4,667,814 A | 5/1987 | Wakamatsu et al. |

(Continued)

FOREIGN PATENT DOCUMENTS

JP 58-148759 9/1983

(Continued)

OTHER PUBLICATIONS

Guidance for Industry-Metered Dose Inhaler (MDI) and Dry Inhaler (DPI) Drug Products, U.S. Department of Health and Human Services, Food and Drug Administration, Center for Drug Evaluation and Research (CDER), Oct. 1998.

(Continued)

*Primary Examiner*—David T. Fidel
*Assistant Examiner*—Jerrold Johnson
(74) *Attorney, Agent, or Firm*—Paul R. Darkes (57) ABSTRACT

A method for maintaining the enclosed volume of a sealed package at about ambient pressure, wherein the package contains a pressurized container comprising a drug, and an HFA (hydrofluoroalkane) propellant selected from the group consisting of HFA 134a and HFA p227, or a mixture thereof; wherein the method comprises the steps of (1) positioning an effective amount of a HFA adsorbent material, and said pressurized container, within a sealable package; (2) sealing the package so that the pressurized container and adsorbent are in an enclosed volume within the package at a pressure equal to about ambient pressure; and (3) adsorbing any leakage of the HFA propellant into the HFA adsorbent material so as to maintain the enclosed volume at about ambient pressure.

30 Claims, 6 Drawing Sheets

U.S. PATENT DOCUMENTS

| | | | |
|---|---|---|---|
| 4,702,963 A | 10/1987 | Phillips et al. | |
| 4,971,196 A | 11/1990 | Kitamura et al. | |
| 5,221,566 A | 6/1993 | Tokoh et al. | |
| 5,300,138 A | 4/1994 | Fischer et al. | |
| 5,322,161 A | 6/1994 | Shichman et al. | |
| 5,567,488 A | 10/1996 | Allen et al. | |
| 5,657,748 A | 8/1997 | Braithwaite | |
| 5,911,937 A | 6/1999 | Hekal | |
| 6,050,400 A | 4/2000 | Taskis et al. | |
| 6,103,141 A | 8/2000 | Incorvia et al. | |
| 6,179,118 B1 * | 1/2001 | Garrill et al. | 206/204 |
| 6,306,503 B1 | 10/2001 | Tsai | |
| 6,315,112 B1 | 11/2001 | Garrill et al. | |
| 6,316,521 B1 | 11/2001 | Disch et al. | |
| 2003/0140923 A1 | 7/2003 | Taylor et al. | |

FOREIGN PATENT DOCUMENTS

| | | |
|---|---|---|
| WO | WO 93/11938 | 6/1993 |
| WO | WO 03/043905 | 5/2003 |

OTHER PUBLICATIONS

Guidance for Industry-Submission of Documentation in Drug Applications for Container Closure Systems Used for the Packaging of Human Drugs and Biologics, U.S. Department of Health and Human Services, Food and Drug Administration; Center for Drug Evaluation and REsearch (CDER) and Center for Biologics Evaluation and Research (CBER), Jun. 1997.

* cited by examiner

METHOD AND PACKAGING FOR PRESSURIZED CONTAINERS

FIELD OF THE INVENTION

This invention relates to a method and a package for packaging pressurized containers suitable for relatively long-term storage. More particularly, it relates to a package and packaging method that utilizes an HFA adsorbent material, such as a molecular sieve, to absorb or adsorb propellant gases gradually leaked out from a pressurized containers, whereby preventing the propellant gas from inflating the package.

BACKGROUND OF THE INVENTION

Pressurized containers such as inhalers may need to be packed in impermeable packages to prevent atmospheric moisture ingress. The use of such impermeable packages can cause accumulation of propellant gases that gradually leak from the pressurized container and may eventually lead to failure of the seals of the package. This problem becomes more prominent when traditional propellants chlorofluorocarbons (CFCs) are replaced by hydrofluoroalkane propellants (such as HFA-134a and HFA-227) for environmental reasons.

U.S. patent Nos. 6,179,118B1, 6,119,853 and 6,352,152 address this problem by using a flexible package that is "impermeable to moisture and permeable to the propellant." While this appears to be a good approach, applicants had much difficulty in fabricating a flexible wrapping material which is impermeable to moisture and permeable to the propellant so that the resulting package would operate similar to "a virtual one-way valve". Presumably, fabricating such flexible wrapping materials is much more technically involved and more costly than it appears from reading the aforementioned patents. Therefore, there is a need for a simpler and more understandable way to solve the inflation problem in packing pressurized containers.

Furthermore, the ability of the packages disclosed in U.S. Pat. Nos. 6,179,118 B1, 6,119,853 and 6,352,152, to prevent gas build up in the packages, would appear to be limited by the permeability of the wrapping material to the propellant and the rate at which the propellant is released from the container.

Therefore, there is a need for an enhanced drug product comprising a package that is impermeable, or substantially impermeable, to the egress of HFA gas from within the package, and still is capable of maintaining the enclosed volume of the sealed package at about ambient pressure when any leakage of HFA gas propellant occurs.

SUMMARY OF THE INVENTION

A primary object of the present invention is to provide a new package for pressurized inhalers, which will reduce or eliminate the inflation problems normally associated with conventional packaging methods. Another object of the present invention is to provide simpler method for solving the inflation problem than the prior art approaches. Another object of the present invention is to provide a new package for pressurized inhalers, which will reduce or eliminate the egress of HFA gas propellant from within the package, normally associated with conventional packaging methods. A further object of the present invention is to provide a method for maintaining the enclosed volume of a sealed package at about ambient pressure, wherein the package contains leakage from a pressurized container comprising an HFA (hydrofluoroalkane) propellant.

It is believed that the mechanism by which the HFA adsorbent material prevents package from inflating is by entrapping the propellant gases gradually leaked from the pressurized container.

The various features of novelty which characterize the invention are pointed out with particularity in the claims annexed to and forming a part of this disclosure. For a better understanding of the invention, its operating advantages, and specific objects attained by its use, reference should be made to the drawings and the following description in which there are illustrated, and described, preferred embodiments of the invention.

DETAILED DESCRIPTION OF THE PREFERRED EMBODIMENTS (1) In a first embodiment, the invention provides, a method for maintaining the enclosed volume of a sealed package at about ambient pressure, wherein the package contains a pressurized MDI (metered dose inhaler) container comprising a drug, and an HFA (hydrofluoroalkane) propellant selected from the group consisting of HFA 134a and HFA p227, or a mixture thereof; wherein the method comprises the steps of:

(i) positioning an effective amount of a HFA adsorbent material, and said pressurized container, within a sealable package;

(ii) sealing the package so that the pressurized container and adsorbent are in an enclosed volume within the package at a pressure equal to about ambient pressure; and (iii) adsorbing any leakage of the HFA propellant into the HFA adsorbent material so as to maintain the enclosed volume at about ambient pressure.

(2) In another embodiment, the invention provides a method according to embodiment (1), wherein the drug is selected from the group consisting of bronchodilators, antihistamines, lung surfactants, antiviral agents, corticosteroids, ant-inflammatory agents, anti-cholinergics, and anti-bacterial agents.

(3) In another embodiment, the invention provides method according to embodiment (1) or (2), wherein the pressurized MDI (metered dose inhaler) container further comprises one or more excipients selected from the group consisting of surfactants, preservatives, flavorings, antioxidants, anti-aggregating agents and co-solvents.

(4) In another embodiment, the invention provides a method according to any one of embodiments (1) to (3), wherein the HFA propellant is HFA 134a.

(5) In another embodiment, the invention provides a method according to any one of embodiments (1) to (3), wherein the HFA propellant is HFA p227.

(6) In another embodiment, the invention provides a method according to any one of embodiments (1) to (5), wherein the HFA adsorbent material is capable of adsorbing the HFA propellant up to about 25% of the weight of the adsorbent.

(7) In another embodiment, the invention provides a method according to any one of embodiments (1) to (5), wherein the HFA gas adsorbent material is capable of adsorbing the HFA propellant up about 20% of the weight of the adsorbent.

(8) In another embodiment, the invention provides a method according to any one of embodiments (1) to (7), wherein the HFA adsorbent material comprises material selected from the group consisting of molecular sieves, activated clays, activated alumina, silica, zeolites, bauxites, and mixtures thereof.

(9) In another embodiment, the invention provides a method according to embodiment (8), wherein the HFA adsorbent material is 10 Å (Angstrom) molecular sieves.

(10) In another embodiment, the invention provides a method according to embodiment (9), wherein the molecular sieves, in an amount of about 4 grams, absorbs about 230 ml of HFA p227.

(11) In another embodiment, the invention provides a method according to embodiment (9), wherein the molecular sieves, in an amount of about 4 grams, absorbs about 230 ml of HFA 134a.

(12) In another embodiment, the invention provides a method according to anyone of embodiments (1) to (11), wherein the package is impermeable to HFA 134a.

(13) In another embodiment, the invention provides a method according to anyone of embodiments (1) to (12), wherein the package is impermeable to HFA p227.

(14) In another embodiment, the invention provides a method according to anyone of embodiments (1) to (12), wherein the package is permeable to HFA p227.

(15) In another embodiment, the invention provides a method according to embodiment (14), wherein the package has a permeability to HFA p227 that is less than or equal to about 0.25 cc of HFA p227 per square meter of package per day at about 1 bar pressure and about room temperature.

(16) In another embodiment, the invention provides a method according to embodiment (14), wherein the package has a permeability to HFA p227 that is less than or equal to about 0.15 cc of HFA p227 per square meter of package per day at about 1 bar pressure and about room temperature.

(17) In another embodiment, the invention provides a method according to embodiment (14), wherein the package has a permeability to HFA p227 that is less than or equal to about 0.10 cc of HFA p227 per square meter of package per day at about 1 bar pressure and about room temperature.

(18) In another embodiment, the invention provides a method according to embodiment (14), wherein the package has a permeability to HFA p227 that is less than or equal to about 0.05 cc of HFA p227 per square meter of package per day at about 1 bar pressure and about room temperature.

(19) In another embodiment, the invention provides a method according to any one of embodiments (1) to (11) or (14), wherein the package is permeable to HFA 134a.

(20) In another embodiment, the invention provides a method according to embodiment (19), wherein the package has a permeability to HFA 134a that is less than or equal to about 4.1 cc of HFA 134a per square meter of package per day at about 1 bar pressure and about room temperature.

(21) In another embodiment, the invention provides a method according to embodiment (19), wherein the package has a permeability to HFA 134a that is less than or equal to about 3.5 cc of HFA 134a per square meter of package per day at about 1 bar pressure and about room temperature.

(22) In another embodiment, the invention provides a method according to embodiment (19), wherein the package has a permeability to HFA 134a that is less than or equal to about 2.5 cc of HFA 134a per square meter of package per day at about 1 bar pressure and about room temperature.

(23) In another embodiment, the invention provides a method according to embodiment (19), wherein the package has a permeability to HFA 134a that is less than or equal to about 1.5 cc of HFA 134a per square meter of package per day at about 1 bar pressure and about room temperature.

(24) In another embodiment, the invention provides a method according to embodiment (19), wherein the package has a permeability to HFA 134a that is less than or equal to about 1.0 cc of HFA 134a per square meter of package per day at about 1 bar pressure and about room temperature.

(25) In another embodiment, the invention provides a method according to embodiment (19), wherein the package has a permeability to HFA 134a that is less than or equal to about 0.5. cc of HFA 134a per square meter of package per day at about 1 bar pressure and about room temperature.

(26) In another embodiment, the invention provides a method according to any one of embodiments (1) to (25), wherein the package is made of metal, glass, or plastic, and is selected from the group consisting of bottles, bags, drum boxes, and irregularly shaped containers.

(27) In another embodiment, the invention provides a method according to any one of embodiments (1) to (26), wherein the package is made of plastic.

(28) In another embodiment, the invention provides a method according to embodiment (27) wherein the plastic is a flexible laminate having a barrier layer providing said package with permeability to HFA 134a and/or HFA p227.

(29) In another embodiment, the invention provides a method according to embodiment (27), wherein the plastic is a flexible laminate having a barrier layer providing said package with impermeability to HFA 134a and/or HFA p227.

(30) In another embodiment, the invention provides a method according to embodiment (28) or (29), wherein said flexible laminate has three layers: polyester/aluminum/polyethylene, wherein the aluminum layer is between the polyester and polyethylene layers.

(31) In another embodiment, the invention provides a method according to embodiment (28) or (29), wherein said barrier layer is made of aluminum foil.

(32) In another embodiment, the invention provides a method according to any one of embodiments (1) to (31), wherein the sealed package is hermetically sealed by heat-sealing, gluing, welding, brazing, mechanical closures or clamps, or compression.

(33) In another embodiment, the invention provides a use of an HFA adsorbent to maintain the pressure of an enclosed volume within a sealed package at about ambient pressure, wherein the sealed package comprises:

(i) a pressurized MDI (metered dose inhaler) container comprising a drug, a HFA (hydrofluoroalkane) propellant selected from the group consisting of HFA 134a and HFA p227, or a mixture thereof;

(ii) an effective amount of an HFA adsorbent material;
wherein the pressurized MDI container and HFA adsorbent material are within the enclosed volume of the sealed package.

(34) In another embodiment, the invention provides a use according to embodiment (33), wherein the drug is selected from the group consisting of bronchodilators, antihistamines, lung surfactants, antiviral agents, corticosteroids, ant-inflammatory agents, anti-cholinergics, and antibiotics.

(35) In another embodiment, the invention provides a use according to embodiment (33) or (34), wherein the pressurized MDI (metered dose inhaler) container further comprises one or more excipients selected from the group consisting of surfactants, preservatives, flavorings, antioxidants, anti-aggregating agents and co-solvents.

(36) In another embodiment, the invention provides a use according to any one of embodiments (33) to (35), wherein the HFA propellant is HFA 134a.

(37) In another embodiment, the invention provides a use according to any one of embodiments (33) to (35), wherein the HFA propellant is HFA p227.

(38) In another embodiment, the invention provides a use according to any one of embodiments (33) to (37), wherein the HFA adsorbent material is capable of adsorbing the HFA propellant up to about 25% of the weight of the adsorbent.

(39) In another embodiment, the invention provides a use according to any one of embodiments (33) to (37), wherein the HFA gas adsorbent material is capable of adsorbing the HFA propellant up about 20% of the weight of the adsorbent.

(40) In another embodiment, the invention provides a use according to any one of embodiments (33) to (39), wherein the HFA adsorbent material comprises material selected from the group consisting of molecular sieves, activated clays, activated alumina, silica, zeolites, bauxites, and mixtures thereof.

(41) In another embodiment, the invention provides a use according to embodiment (40) wherein the HFA adsorbent material is 10 Å (Angstrom) molecular sieves.

(42) In another embodiment, the invention provides a use according to embodiment (41), wherein the molecular sieves, in an amount of about 4 grams, absorbs about 230 ml of HFA p227.

(43) In another embodiment, the invention provides a use according to embodiment (41), wherein the molecular sieves, in an amount of about 4 grams, absorbs about 230 ml of HFA 134a.

(44) In another embodiment, the invention provides a use according to any one of embodiments (33) to (43), wherein the package is impermeable to HFA 134a.

(45) In another embodiment, the invention provides a use according to any one of embodiments (33) to (42), wherein the package is impermeable to HFA p227.

(46) In another embodiment, the invention provides a use according to any one of embodiments (33) to (42), wherein the package is permeable to HFA p227.

(47) In another embodiment, the invention provides a use according to embodiment (46), wherein the package has a permeability to HFA p227 that is less than or equal to about 0.25 cc of HFA p227 per square meter of package per day at about 1 bar pressure and about room temperature.

(48) In another embodiment, the invention provides a use according to embodiment (46), wherein the package has a permeability to HFA p227 that is less than or equal to about 0.15 cc of HFA p227 per square meter of package per day at about 1 bar pressure and about room temperature.

(49) In another embodiment, the invention provides a use according to embodiment (46), wherein the package has a permeability to HFA p227 that is less than or equal to about 0.10 cc of HFA p227 per square meter of package per day at about 1 bar pressure and about room temperature.

(50) In another embodiment, the invention provides a use according to embodiment (46), wherein the package has a permeability to HFA p227 that is less than or equal to about 0.05 cc of HFA p227 per square meter of package per day at about 1 bar pressure and about room temperature.

(51) In another embodiment, the invention provides a use according to anyone of embodiments (33) to (43), wherein the package is permeable to HFA 134a.

(52) In another embodiment, the invention provides a use according to embodiment (51), wherein the package has a permeability to HFA 134a that is less than or equal to about 4.1 cc of HFA 134a per square meter of package per day at about 1 bar pressure and about room temperature.

(53) In another embodiment, the invention provides a use according to embodiment (51), wherein the package has a permeability to HFA 134a that is less than or equal to about 3.5 cc of HFA 134a per square meter of package per day at about 1 bar pressure and about room temperature.

(54) In another embodiment, the invention provides a use according to embodiment (51), wherein the package has a permeability to HFA 134a that is less than or equal to about 2.5 cc of HFA 134a per square meter of package per day at about 1 bar pressure and about room temperature.

(55) In another embodiment, the invention provides a use according to embodiment (51), wherein the package has a permeability to HFA 134a that is less than or equal to about 1.5 cc of HFA 134a per square meter of package per day at about 1 bar pressure and about room temperature.

(56) In another embodiment, the invention provides a use according to embodiment (51), wherein the package has a permeability to HFA 134a that is less than or equal to about 1.0 cc of HFA 134a per square meter of package per day at about 1 bar pressure and about room temperature.

(57) In another embodiment, the invention provides a use according to embodiment (51), wherein the package has a permeability to HFA 134a that is less than or equal to about 0.5 cc of HFA 134a per square meter of package per day at about 1 bar pressure and about room temperature.

(58) In another embodiment, the invention provides a use according to any one of embodiments (33) to (57), wherein the package is made of metal, glass, or plastic, and is selected from the group consisting of bottles, bags, drum boxes, and irregularly shaped containers.

(59) In another embodiment, the invention provides a use according to embodiment (58), wherein the package is made of plastic.

(60) In another embodiment, the invention provides a use according to embodiment (59), wherein the plastic is a flexible laminate having a barrier layer providing said package with impermeability to HFA 134a and/or HFA p227.

(61) In another embodiment, the invention provides a use according to embodiment (59) or (60), wherein the plastic is a flexible laminate having a barrier layer providing said package with permeability to HFA 134a and/or HFA p227.

(62) In another embodiment, the invention provides a use according to embodiment (60) or (61), wherein said flexible laminate has three layers: polyester/aluminum/polyethylene, wherein the aluminum layer is between the polyester and polyethylene layers.

(63) In another embodiment, the invention provides a use according to embodiment (60) or (61), wherein said barrier layer is made of aluminum foil.

(64) In another embodiment, the invention provides a use according to any one of embodiments (33) to (63), wherein the sealed package is hermetically sealed by heat-sealing, gluing, welding, brazing, mechanical closures or clamps, or compression.

(65) In another embodiment, the invention provides a pharmaceutical product comprising:

(i) a pressurized MDI (metered dose inhaler) container comprising a drug, and an HFA (hydrofluoroalkane) propellant selected from the group consisting of HFA 134a and HFA p227, or a mixture thereof;

(ii) an effective amount of an HFA adsorbent material; and (iii) a sealed package having an enclosed volume within which the pressurized container and the HFA adsorbent material are situated, wherein the sealed package is impermeable to the HFA propellant and the pressure within the enclosed volume of the package is equal to about ambient pressure; and wherein the HFA adsorbent material is capable of adsorbing the HFA propellant so as to maintain a constant pressure within said enclosed volume, when any leakage of the HFA propellant occurs from the pressurized container.

(66) In another embodiment, the invention provides a pharmaceutical product according to embodiment (65), wherein the drug is selected from the group consisting of bronchodilators, antihistamines, lung surfactants, antiviral agents, corticosteroids, ant-inflammatory agents, anti-cholinergics, and antibiotics.

(67) In another embodiment, the invention provides a pharmaceutical product according to embodiment (65) or (66), wherein the pressurized MDI (metered dose inhaler) container further comprises one or more excipients selected from the group consisting of surfactants, preservatives, flavorings, antioxidants, anti-aggregating agents and co-solvents.

(68) In another embodiment, the invention provides a pharmaceutical product according to any one of embodiments (65) to (67), wherein the HFA propellant is HFA 134a.

(69) In another embodiment, the invention provides a pharmaceutical product according to any one of embodiments (65) to (67), wherein the HFA propellant is HFA p227.

(70) In another embodiment, the invention provides a pharmaceutical product according to any one of embodiments (65) to (69), wherein the HFA adsorbent material is capable of adsorbing the HFA propellant up to about 25% of the weight of the adsorbent.

(71) In another embodiment, the invention provides a pharmaceutical product according to any one of embodiments (65) to (69), wherein the HFA gas adsorbent material is capable of adsorbing the HFA propellant up about 20% of the weight of the adsorbent.

(72) In another embodiment, the invention provides a pharmaceutical product according to any one of embodiments (65) to (71), wherein the HFA adsorbent material comprises material selected from the group consisting of molecular sieves, activated clays, activated alumina, silica, zeolites, bauxites, and mixtures thereof.

(73) In another embodiment, the invention provides a pharmaceutical product according to embodiment (72), wherein the HFA adsorbent material is 10 Å (Angstrom) molecular sieves.

(74) In another embodiment, the invention provides a pharmaceutical product according to embodiment (73), wherein the molecular sieves, in an amount of about 4 grams, absorbs about 230 ml of HFA p227.

(75) In another embodiment, the invention provides a pharmaceutical product according to embodiment (73), wherein the molecular sieves, in an amount of about 4 grams, absorbs about 230 ml of HFA 134a.

(76) In another embodiment, the invention provides a pharmaceutical product according to any one of embodiments (65) to (75), wherein the package is impermeable to HFA 134a.

(77) In another embodiment, the invention provides a pharmaceutical product according to any one of embodiments (65) to (76), wherein the package is impermeable to HFA p227.

(78) In another embodiment, the invention provides a pharmaceutical product according to any one of embodiments (65) to (77), wherein the package is made of metal, glass, or plastic, and is selected from the group consisting of bottles, bags, drum boxes, and irregularly shaped containers.

(79) In another embodiment, the invention provides a pharmaceutical product according to embodiment (71), wherein the package is made of plastic.

(80) In another embodiment, the invention provides a pharmaceutical product according to embodiment (79), wherein the plastic is a flexible laminate having a barrier layer providing said package with impermeability to HFA 134a and/or HFA p227.

(81) In another embodiment, the invention provides a pharmaceutical product according to embodiment (80), wherein said flexible laminate has three layers: polyester/aluminum/polyethylene, wherein the aluminum layer is between the polyester and polyethylene layers.

(82) In another embodiment, the invention provides a pharmaceutical product according to embodiment (80), wherein said barrier layer is made of aluminum foil.

(83) In another embodiment, the invention provides a pharmaceutical product according to any one of embodiments (65) to (82), wherein the sealed package is hermetically sealed by heat-sealing, gluing, welding, brazing, mechanical closures or clamps, or compression.

(84) A pharmaceutical product comprising:

(i) a pressurized MDI (metered dose inhaler) container comprising a drug, and an HFA (hydrofluoroalkane) propellant selected from the group consisting of HFA 134a and HFA p227, or a mixture thereof;

(ii) an effective amount of an HFA adsorbent material; and (iii) a sealed package having an enclosed volume within which the pressurized container and the HFA adsorbent material are situated, wherein the pressure within the enclosed volume of the package is equal to about ambient pressure;

wherein the HFA adsorbent material is capable of adsorbing the HFA propellant so as to maintain a constant pressure within said enclosed volume, when any leakage of the HFA propellant occurs from the pressurized container; and wherein the package has a permeability to HFA p227 that is less than or equal to about 0.25 cc of HFA p227 per square meter of package per day at about 1 bar pressure and about room temperature, or a permeability to HFA 134a that is less than or equal to about 4.1 cc of HFA 134a per square meter of package per day at about 1 bar pressure and about room temperature.

(85) A pharmaceutical product according to embodiment (84), wherein the package has a permeability to HFA p227 that is less than or equal to about 0.15 cc of HFA p227 per square meter of package per day at about 1 bar pressure and about room temperature.

(86) A pharmaceutical product according to embodiment (84), wherein the package has a permeability to HFA p227 that is less than or equal to about 0.10 cc of HFA p227 per square meter of package per day at about 1 bar pressure and about room temperature.

(87) A pharmaceutical product according to embodiment (84), wherein the package has a permeability to HFA p227 that is less than or equal to about 0.05 cc of HFA p227 per square meter of package per day at about 1 bar pressure and about room temperature.

(88) A pharmaceutical product according to embodiment (84), wherein the package has a permeability to HFA 134a that is less than or equal to about 3.5 cc of HFA 134a per square meter of package per day at about 1 bar pressure and about room temperature.

(89) A pharmaceutical product according to embodiment (84), wherein the package has a permeability to HFA 134a that is less than or equal to about 2.5 cc of HFA 134a per square meter of package per day at about 1 bar pressure and about room temperature.

(90) A pharmaceutical product according to embodiment (84), wherein the package has a permeability to HFA 134a that is less than or equal to about 1.5 cc of HFA 134a per square meter of package per day at about 1 bar pressure and about room temperature.

(91) A pharmaceutical product according to embodiment (84), wherein the package has a permeability to HFA 134a that is less than or equal to about 1.0 cc of HFA 134a per square meter of package per day at about 1 bar pressure and about room temperature.

(92) A pharmaceutical product according to embodiment (84), wherein the package has a permeability to HFA 134a that is less than or equal to about 0.5 cc of HFA 134a per square meter of package per day at about 1 bar pressure and about room temperature.

(93) In another embodiment, the invention provides a pharmaceutical product according to any one of embodiments (84) to (92), wherein the drug is selected from the group consisting of bronchodilators, antihistamines, lung surfactants, antiviral agents, corticosteroids, ant-inflammatory agents, anti-cholinergics, and antibiotics.

(94) In another embodiment, the invention provides a pharmaceutical product according to any one of embodiments (84) to (93), wherein the pressurized MDI (metered dose inhaler) container further comprises one or more excipients selected from the group consisting of surfactants, preservatives, flavorings, antioxidants, anti-aggregating agents and co-solvents.

(95) In another embodiment, the invention provides a pharmaceutical product according to any one of embodiments (84) to (94), wherein the HFA propellant is HFA 134a.

(96) In another embodiment, the invention provides a pharmaceutical product according to any one of embodiments (84) to (94), wherein the HFA propellant is HFA p227.

(97) In another embodiment, the invention provides a pharmaceutical product according to any one of embodiments (84) to (96), wherein the HFA adsorbent material is capable of adsorbing the HFA propellant up to about 25% of the weight of the adsorbent.

(98) In another embodiment, the invention provides a pharmaceutical product according to any one of embodiments (84) to (96), wherein the HFA gas adsorbent material is capable of adsorbing the HFA propellant up about 20% of the weight of the adsorbent.

(99) In another embodiment, the invention provides a pharmaceutical product according to any one of embodiments (84) to (98), wherein the HFA adsorbent material comprises material selected from the group consisting of molecular sieves, activated clays, activated alumina, silica, zeolites, bauxites, and mixtures thereof.

(100) In another embodiment, the invention provides a pharmaceutical product according to embodiment (99), wherein the HFA adsorbent material is 10 Å (Angstrom) molecular sieves.

(101) In another embodiment, the invention provides a pharmaceutical product according to embodiment (100), wherein the molecular sieves, in an amount of about 4 grams, absorbs about 230 ml of HFA p227.

(102) In another embodiment, the invention provides a pharmaceutical product according to embodiment (100), wherein the molecular sieves, in an amount of about 4 grams, absorbs about 230 ml of HFA 134a.

(103) In another embodiment, the invention provides a pharmaceutical product according to any one of embodiments (84) to (102), wherein the package is made of metal, glass, or plastic, and is selected from the group consisting of bottles, bags, drum boxes, and irregularly shaped containers.

(104) In another embodiment, the invention provides a pharmaceutical product according to embodiment (103), wherein the package is made of plastic.

(105) In another embodiment, the invention provides a pharmaceutical product according to embodiment (104), wherein the plastic is a flexible laminate having a barrier layer providing said package with permeability to HFA 134a and/or HFA p227.

(106) In another embodiment, the invention provides a pharmaceutical product according to embodiment (105), wherein said flexible laminate has three layers: polyester/aluminum/polyethylene, wherein the aluminum layer is between the polyester and polyethylene layers.

(107) In another embodiment, the invention provides a pharmaceutical product according to embodiment (105), wherein said barrier layer is made of aluminum foil.

(108) In another embodiment, the invention provides a pharmaceutical product according to any one of embodiments (84) to (107), wherein the sealed package is hermetically sealed by heat-sealing, gluing, welding, brazing, mechanical closures or clamps, or compression.

(109) In another embodiment, the invention provides a flexible laminate according to any one of embodiments (30), (62), (81), and (106) comprising 12 micron polyester/9 micron aluminum foil/50 micron polyethylene.

It is appreciated that certain features of the invention, which are, for clarity, described in the context of separate embodiments, may also be provided in combination in a single embodiment. Also, various features of the invention which are, for brevity, described in the context of a single embodiment, may also be provided separately or in any suitable subcombination.

The Ability of HFA Adsorbents to Entrap Propellants

It is discovered that HFA adsorbent materials, especially molecular sieves, are capable of removing (by entrapping) propellant gases from local environment. The present invention takes advantage of this property of the HFA adsorbent materials and enclose them in an impermeable, or substantially impermeable, flexible package as a means to preventing the leaked out propellant from inflating the package. By enclosing one or more HFA adsorbent materials in the package to absorb or adsorb any leaked-out propellant, applicants can make the flexible wrapping material as impermeable as possible to prevent moisture ingress without worrying about the leaked-out propellant inflating and causing failure of the seals in the flexible package. To determine the proper type and amount of HFA adsorbent material to be used in each package for a pressurized inhaler containing a specific propellant, applicants conducted the following measurement and determined that about 4 grams of a sachet of 10 Angstrom molecular sieves can remove (adsorb) approximately 230 ml of HFA-227 propellant.

Two methods are used to measure the absorption capability of the sieves. The Initial Measurement method uses flowrap packs containing active product to obtain an approximate data on the amount of propellant that would be absorbed. The Precise Measurement method builds on the results obtained from the Initial Measurement method but uses containers filled only with propellant for the purpose of eliminating any possible effect from the active compounds (i.e., medicaments).

For the Initial Measurement method, a number of sample packs (flexible package enclosing a pressurized inhaler containing HFA-227 propellant and the molecular sieve to be tested) are obtained and checked for seal integrity by testing on the Qualitek leak tester. The packs were orientated with the valve of the pressurized inhaler on the top. With minimum disturbance, the orientation of the packs is reversed (with the valve pointing downwards) and the aerosol fired for a predetermined number of shots and the time taken to deflate each of the packs was recorded. The reason for these precautions is to minimize active product expelled with propellant, which may coat the sieves and possibly reduce their absorption capacity. The packs are then opened and the sieves are examined for the presence of the active product on their surfaces. The presence of the active product would indicate that inverting has not prevented the active product from being expelled and consequently it could have effected the absorption rate. The results of the Initial Measurement are as follows:

All packs with up to 15 shots fired return to original size within 10 minutes, while packs with 20 shorts fired show slight inflation after 15 minutes. Examination of the sieves used showed evidence of product deposition on the inside of the pouch and on the outside of the adsorbent sachet although none could be seen on the surface of the adsorbent itself. As such this was considered a good guide to the adsorbent capacity prior to the more precise method being undertaken.

For the Precise Measurement method, the following steps are followed:

1. A number of pressurized inhalers (aerosol cans) filled only with HFA-227 Propellant are obtained. They are numbered and their weights are recorded.
2. A number of flexible packages with a open end are obtained. They are also numbered.
3. Each aerosol can in turn is placed into an actuator and inserted into the flexible package.
4. A predetermined amount of molecular sieves is transferred from an unused polyethylene bag to a smaller minigrip bag. Using tweezers to avoid transfer of moisture, the sieves are weighed and inserted into each of the packages in turn.
5. Each of the packages, now containing an aerosol can and molecular sieves, is immediately heat sealed using a AstraPack Heatsealer that has been set up to produce effective seals with this particular package material. This step is repeated for all the packages.
6. The first five packages remain as sealed. This is for the purpose of assessing the effect of moisture pickup from the actuator and/or the air in the package, which can serve as the base line for all other measurements.
7. The remaining packages are divided into sets of five. The cans of a set are fired for a predetermined number of shots. The maximum number, of shorts is determined based on the information obtained from the Initial Measurement method. Sets with more than 10 shots are given time to deflate before continuing with the next shot. All the sets of packages are stored for a minimum of 24 hours to allow the maximum propellant absorption to occur.
8. The packages are then leak tested using a Qualitek leak tester to ensure all packages have been adequately sealed and hence the data obtained are relevant. Results from packages failing the leak test are discarded.
9. Each package is opened in turn and the sieve and the can are re-weighed. The sieve is weighed first to avoid weight increase due to atmospheric moisture absorption.
10. The weight loss from each can and the weight gain of the sieve are obtained and the average for each set is calculated. The data are then plotted on a graph to show the rate of weight gain by the sieves and the number of shots (and hence the volume of gas) required to reach maximum absorption level. Similarly, the data on the average weight loss from the cans are plotted to show the equivalent transfer of propellant from the cans into the sieves until final absorption for sieves reached (see FIG. 1).

Figure 1:
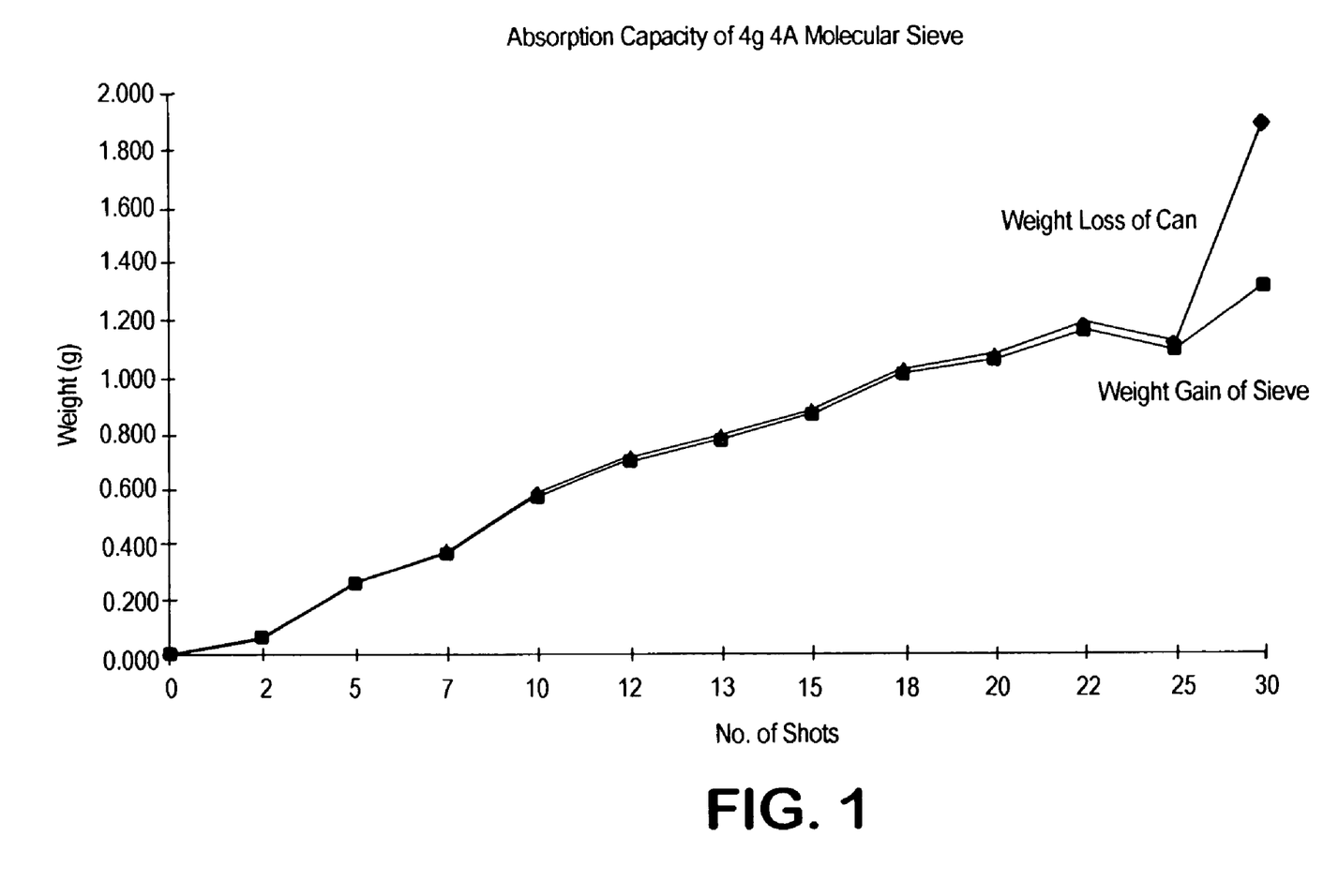
FIG. 1 is a graph summarizing a study that shows that the molecular sieve is an effective HFA adsorbent for entrapping a propellant gas from the air, whereby preventing inflation of the package.

As shown in FIG. 1, comparison of weight gain by the molecular sieve against gas volume indicates a steady rise in weight until about 25 shots (equate to 230 ml) of propellant has been absorbed. This is matched by the weight loss from the cans climbed while the weight of the sieves remained steady. Thus, it is concluded that about a 4 grams sachet of a 10 Angstrom molecular sieve can remove (adsorb) approximately 230 ml of HFA-227 propellant.

Of course, the HFA adsorbent material's capacity to absorb the propellant may vary under actual production line conditions because the HFA adsorbent material may be pre-exposed to the atmosphere for a certain period of time and absorb atmospheric moisture. Absorption of moisture limits the eventual capacity of the HFA adsorbent material to absorb propellant gases. Therefore, it should be taken into consideration in practicing the present invention. In the specific embodiment disclosed herein, applicants first determine the rate at which an HFA adsorbent material absorbs atmospheric moisture under conditions close to actual production line conditions (see FIGS. 2 and 3), then examine the effect of the length of atmospheric exposure on the eventual capacity of propellant adsorption under typical production conditions (see FIGS. 4 and 5). The data from this study are used to determine a time allowance for normal production processes, whilst still always ensuring that the original targeted amount of propellant can be adsorbed.

Figure 2:
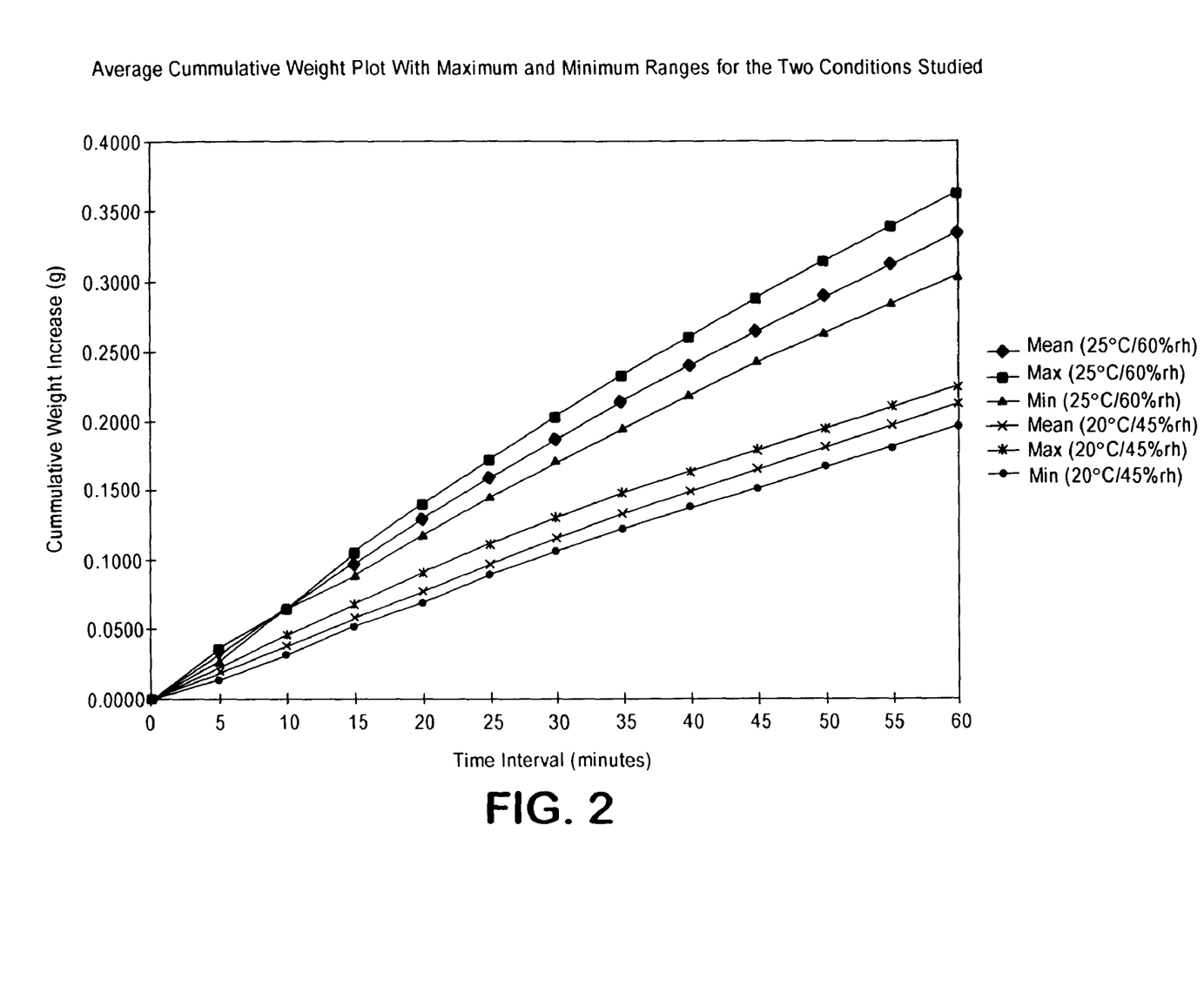
FIG. 2 shows the rate of moisture absorption by the molecular sieves during the first hour of exposure to the atmosphere.
Figure 3:
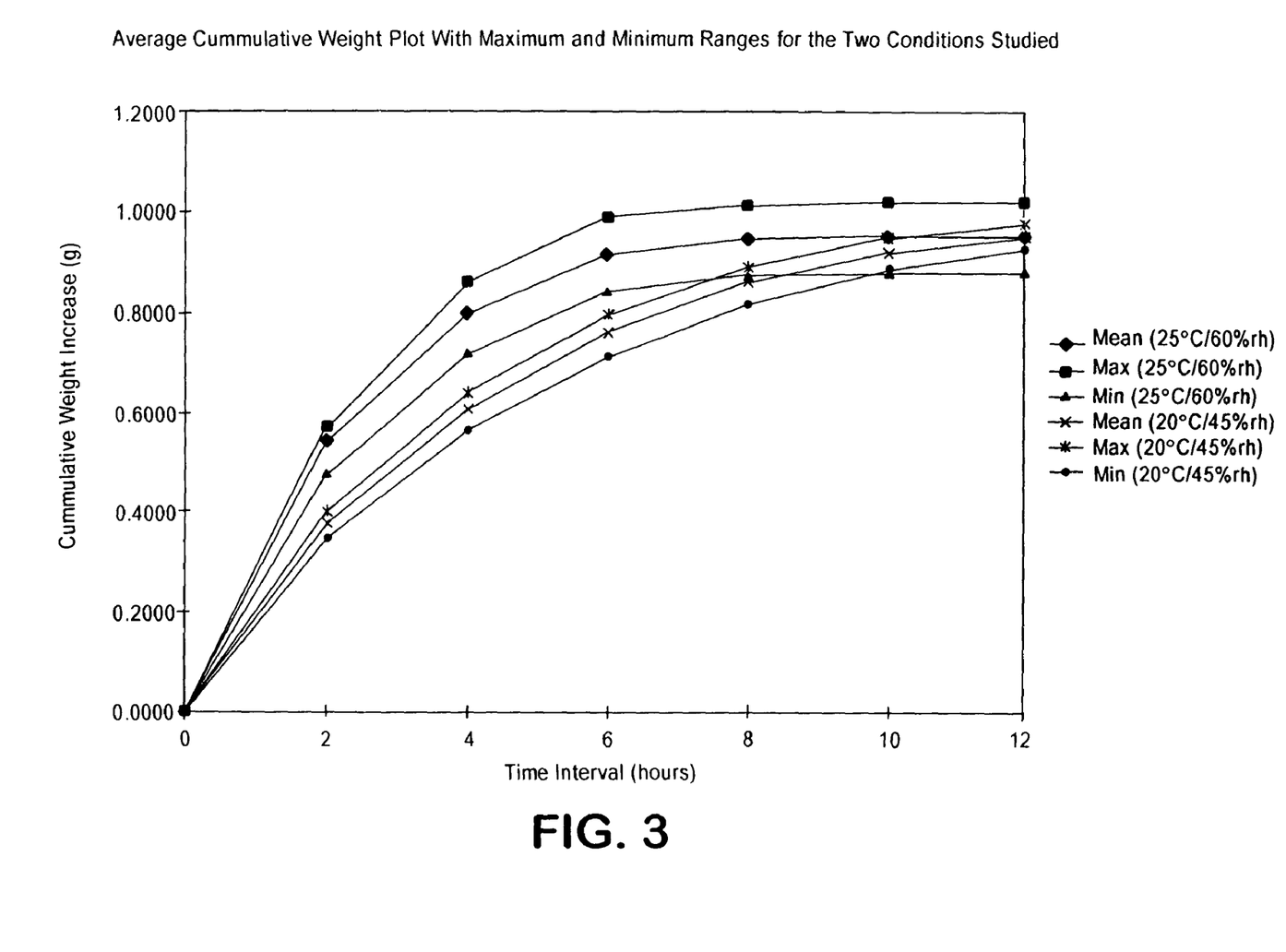
FIG. 3 shows the rate of moister absorption by the same molecular sieves used in FIG. 2 during an exposure period of 12 hours.

As indicated in FIGS. 2 and 3, the moisture absorption during the first hour of exposure can reach 20% of the maximum moisture absorption at 20° C./45% RH (relative humility) and 34% at 25° C./60% RH. Applicants also examined the difference in moisture absorption between the sieves in top and bottom positions of a bulk container found that molecular sieves directly exposed to the atmosphere will absorb moisture much more rapidly than those protected by virtue of being in a lower position in the container. This supports the view that sieves in a reel format will maintain their effectiveness longer. These data will help determine proper procedures of handling molecular sieves in the production environment.

Figure 4:
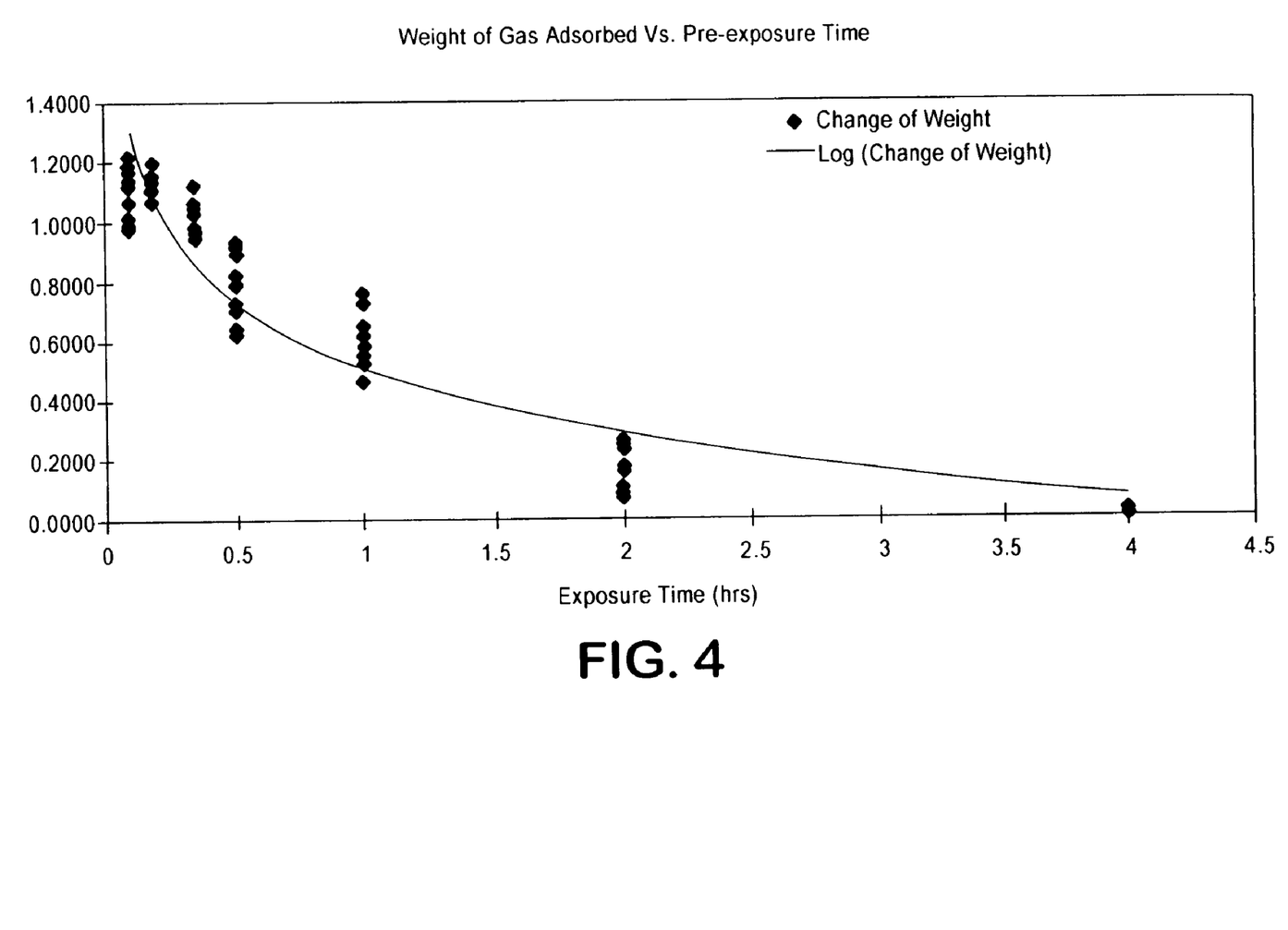
FIGS. 4 and 5 shows that the molecular sieves's capacity for adsorbing. propellant gases is reduced if the sieves are pre-exposed to moisture for different time intervals.
Figure 5:
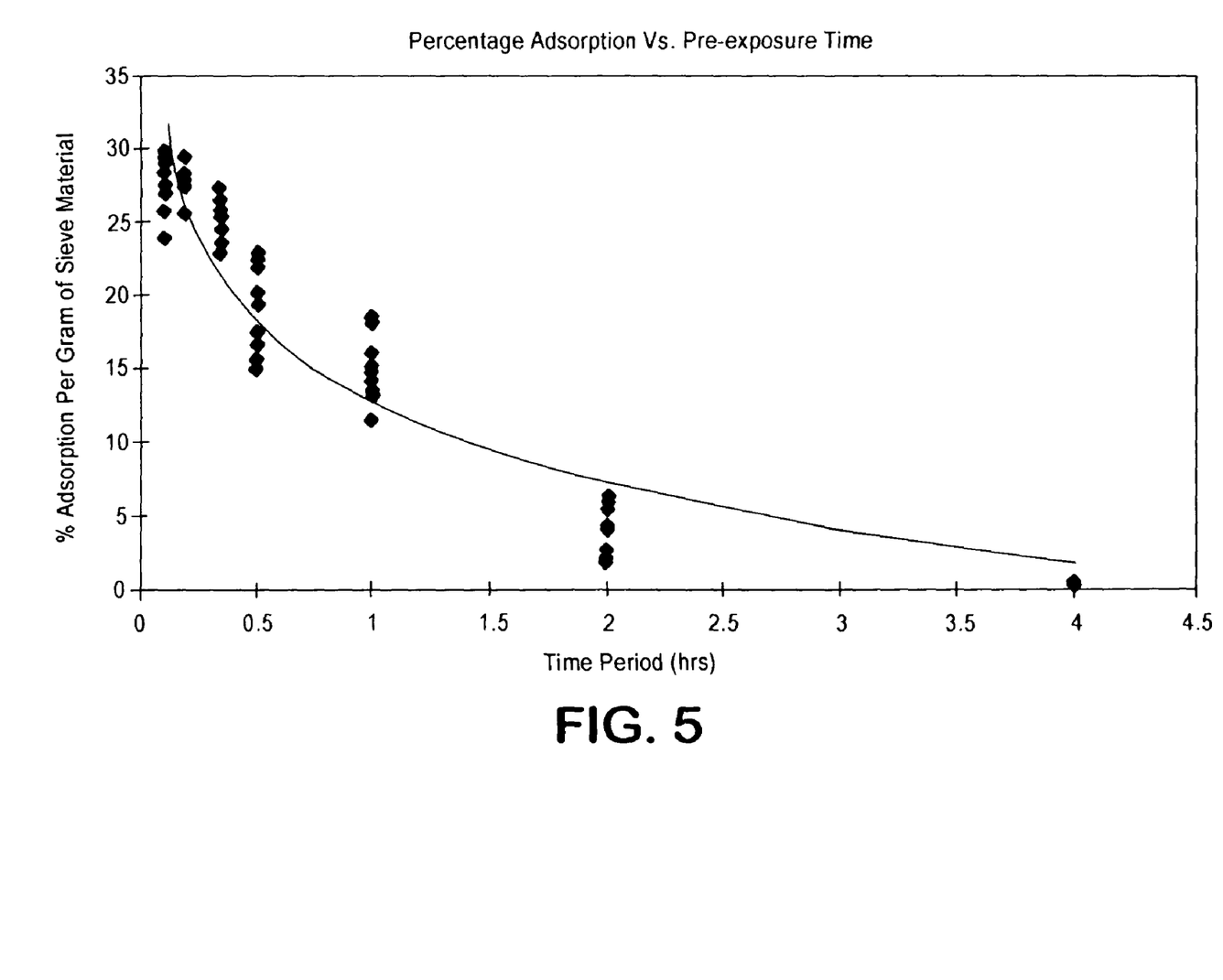

In FIGS. 4 and 5, the molecular sieves are exposed to the production conditions for the prescribed period of time and then immediately packaged using an Astrapack heatsealer. The resulting packs are left for 10 minutes to allow the seals to cool and then the aerosols (filled with propellant only) are actuated 5 times so that the packages expend. The packs are left for another 10 minutes to allow to adsorb the propellant.

The actuating procedure is repeated until each sieve reached its maximum adsorption capacity. At the end of a 24-hour period (a period to ensure maximum adsorption of the propellant), each pack is opened and the sieves are weighed immediately. FIG. 4 shows that the amount (in grams) of propellant adsorbed by 4 grams of the molecular sieves is reduced following exposure to moisture for the different time periods indicated. FIG. 5 shows the percentage propellant adsorption per gram of molecular sieves over the same time periods as in FIG. 4. The goal in this particular case is to adsorb 100 ml of HFA-227 propellant (equivalent to 0.76 g) by using a pouch containing 4 grams of molecular sieves. The data showing in FIGS. 4 and 5 indicate this goal can be achieved even if the sieves are exposed to the normal atmospheric moisture in the production line for 30 minutes.

The above study results demonstrate that inclusion of an HFA adsorbent inside the impermeable, or substantially impermeable, package is a simple, practical and effective solution to the inflation problem of packages for pressurized containers. Particularly, molecular sieves are very effective HFA adsorbent materials against package inflation when used in practicing the present invention.

Although there are various types of HFA adsorbent materials available and their effectiveness against any given propellant may vary considerably, it is understood that people of ordinary skill in the art can easily adopt some conventional assay methods, such as the above-described study, to determine the type and amount of HFA adsorbent material that is effective in reducing package inflation caused by a particular propellant leaked from the pressurized container enclosed in the package.

The Propellants

Propellants for use in the invention mean pharmacologically inert liquids with boiling points from about room temperature (25° C.) to about −25° C. which singly or in combination exert a high vapor pressure at room temperature. Upon activation of the MDI system, the high vapor pressure of the propellant in the MDI forces a metered amount of drug formulation out through the metering valve then the propellant very rapidly vaporizes dispersing the drug particles. The propellants used in the present invention are preferably hydrofluorocarbons or hydrofluoroalkanes such as HFA-134a and HFA-227.

Drugs

The term "drug" as used herein is intended to encompass the presently available pharmaceutically active drugs used therapeutically and further encompasses future developed therapeutically effective drugs that can be administered by the intrapulmonary route. Drugs may be selected from, for example, analgesics, e.g. codeine, dihydromorphine, ergotamine, fentanyl or morphine, anginal preparations, e.g. diltiazem; antiallergics, e.g. cromoglycate, ketotifen or nedocromil; antiinfectives e.g. cephalosporins, penicillins, streptomycin, sulphonamides, tetracyclines pentamidine, and Neuraminidase Inhibitors, such as zanamivir (Relenza®) available from GlaxoSmithkline; and Ribavirin (Virazole®) manufactured by ICN Pharmaceuticals, Inc.; antihistamines, e.g. mnethapyfilene; antitussives, e.g. noscapine; beta-adrenergics that include bronchodilators such as salbutamol, salmeterol, ephedrine, adrenaline, fenoterol, forinoterol, isoprenaline, phenylephrine, phenylpropanolamine, reproterol, rimiterol, terbutaline, isoetharine, tulobuterol, orciprenaline, or (−)4-amino-3,5-dichloro-.alpha.-[[[6-[2-(2-pyridinyl)ethoxy]hexyl]-amino]methyl]benzenemethanol, epinephrine (Primatene), formoterol (Foradil), isoproterenol (Isuprel), isoetharine (Bronkosol), metaproterenol (Alupent, Metaprel), albuterol (Proventil, Ventolin), terbutaline (Bricanyl, Brethine), bitolterol (Tornalate), pirbuterol (Maxair), salmeterol (Serevent), salmeterol+fluticasone combination (Advair Diskus), and albuterol+atrovent combination (Combivent); sodium channel blockers such as amiloride, anticholinergics e.g. ipratropium, atropine or oxftropium; hormones, e.g. cortisone, hydrocordisone or prednisolone; and therapeutic proteins and peptides, e.g. insulin or glucagon; anti-inflammatory drugs used in connection with the treatment of respiratory diseases include steroids such as NASACORT AQ® (triamcinolone acetonide), AZMACORT AQ® (triamcinolone acetonide) flunisolide, fluticasone, budesonide, triamcinolone acetonide, beclomethasone (Vanceril, Beclovent), budesonide (Pulmicort) dexamethasone, flunisolide (Aerobid), fluticasone (Flovent), salmeterol+fluticasone combination (Advair Diskus), and triamcinolone (Azmacort), and Mediator-release inhibitors such as Intal (cromolyn sodium), and nedocromil sodium (Tilade); leukotrine (LT) inhibitors, vasoactive intestinal peptide (VIP), tachykinin antagonists, bradykinin antagonists, endothelin antagonists, heparin furosemide, anti-adhesion molecules, cytokine modulators, biologically active endonucleases, recombinant human (rh) DNase compounds, alpha-antitrypsin and disodium cromoglycate (DSCG); and lung surfactants such as lipid-containing compositions as described in TONGE et. Al, WO 99/09955; Pulmonary surfactants as decribed in Devendra et. Al, Respir Res 2002, 3:19; Infasurf® available from ONY; Curosurf® available from Dey Laboratories; Exosurf® by Glaxo Wellcome; Survanta available from Abbot; Surfaxin® lung surfactant available from Discovery Laboratories.

The present invention is intended to encompass the free acids, free bases, salts, amines and various hydrate forms including semi-hydrate forms of such drugs and is particularly directed towards pharmaceutically acceptable formulations of such drugs which are formulated in combination with pharmaceutically acceptable excipient materials generally known to those skilled in the art, preferably without other additives such as preservatives.

Preferred drug formulations do not include additional components such as preservatives which have a significant effect on the overall formulation. Thus preferred formulations consist essentially of pharmaceutically active drug and a pharmaceutically acceptable carrier (e.g., water and/or ethanol). However, if a drug is liquid without an excipient the formulation may consist essentially of the drug which has a sufficiently low viscosity that it can be aerosolized using a dispenser of the present invention.

Drug Formulations

Drug formulations for use in the invention may be free or substantially free of formulation excipients, e.g., surfactants and cosolvents, etc. Such drug formulations are advantageous since they may be substantially tasteless and odorless, less irritant and less toxic than excipient-containing formulations. Thus, a preferred drug formulation consists essentially of a drug, or a physiologically acceptable salt or solvate thereof, optionally in combination with one or more other pharmacologically active agent, and a hydrofluorocarbon propellant.

Optionally, the aerosol formulations according to the invention may further comprise one or more cosolvent. A polar cosolvent such as $C_{2-6}$ aliphatic alcohols and polyols, e.g., glycerol, ethanol, isopropanol and propylene glycol, preferably ethanol, may be included in the drug formulation in the desired amount, either as the only excipient or in addition to other excipients, such as surfactants. Suitably, the drug formulation may contain 0.01 to 5% w/w based on the propellant of a polar cosolvent, e.g., ethanol, preferably 0.1 to 5% w/w, e.g., about 0.1 to 1% w/w.

Optionally, the aerosol formulations according to the invention may further comprise one or more surfactants. The surfactants must be physiologically acceptable upon administration by inhalation. Within this category are included surfactants such as oleic acid, sorbitan trioleate, sorbitan mono-oleate, sorbitan monolaurate, polyoxyethylene (20) sorbitan monolaurate, polyoxyethylene (20) sorbitan monooleate, natural lecithin, oleyl polyoxyethylene (2) ether, stearyl polyoxyethylene (2) ether, lauryl polyoxyethylene (4) ether, block copolymers of oxyethylene and oxypropylene, synthetic lecithin, diethylene glycol dioleate, tetrahydrofurfuryl oleate, ethyl oleate, isopropyl myristate, glyceryl monooleate, glyceyl monostearate, glyceryl monoricinoleate, cetyl alcohol, stearyl alcohol, polyethylene glycol 400, cetyl pyridinium chloride, benzalkonium chloride, olive oil, glyceryl monolaurate, corn oil, cotton seed oil and sunflower seed oil. Preferred surfactants are lecithin, oleic acid and sorbitan trioleate. The amount of surfactant employed is desirably in the range of 0.0001% to 50% w/w ratio relative to the drug, in particular 0.05 to 5% w/w ratio.

Optionally, the aerosol formulations according to the invention may further comprise one or more stabilizers. The stabilizer is selected from the group consisting of glycin, glycine, alanine, valine, leucine, isoleucine, methionine, threonine, isovaline, phenylalanine, tyrosine, serine, histidine, tryptophan, proline, hydroxyproiine, arginine, ornithine, asparagine, citrulline, aspartic acid, cysteine, glutamic acid, glutamine, lysine, hydroxylysine, N-acetyl-L-cysteine, phenylalanine, trans-4-hydroxy-L-proline, tyrosine, L-aspartyl-L-phenylalanine methylester and a mixture of any of the foregoing.

Optionally, the aerosol formulations according to the invention may further comprise one or more antioxidants. The antioxidant may be selected from the group consisting of tocopherol, deteroxime mesylate, methyl paraben, ethyl paraben and ascorbic acid and mixtures thereof. A preferred antioxidant is tocopherol.

The Package

Figure 6:
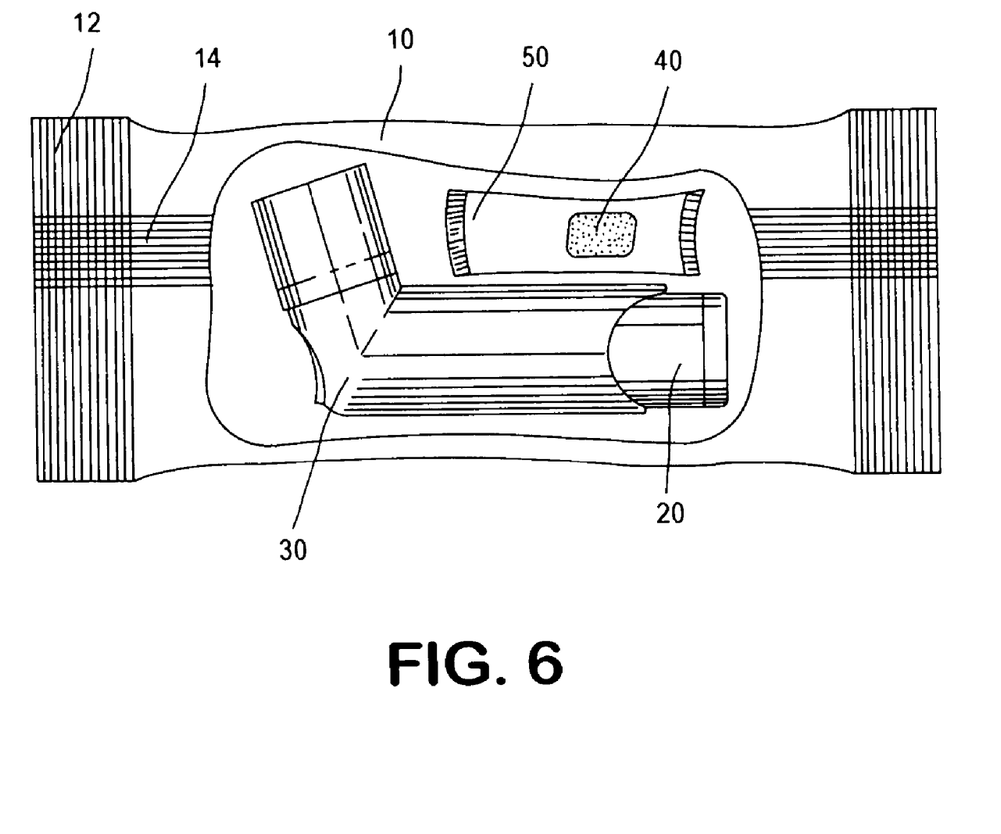
FIG. 6 depicts a typical metered dose (pressurized container) inhaler package according to the present invention.

According to one embodiment of the present invention, shown in FIG. 6, the pharmaceutical product has an impermeable, or substantially impermeable, flexible package 10, in which a metered dose pressurized container 20, inhalation device 30 and a molecular sieve 40 enclosed in a sachet 50, are sealed in an enclosed volume 60.

The flexible package is conventional and its manufacturing is well within the knowledge of the people skilled in the art. In general, the package is constructed from flat reels of laminate which are folded or otherwise formed according to the packaging equipment technology into a package by means of sealing and cutting. In this embodiment the package is constructed from a flat reel of flexible material which is curled around into a long tube and a seal 14 is formed by heating (welding) the edges of the tube together. The cross seals 12 are formed by a straight heater bar which clamps the laminate tube before and after the package contents (i.e., the inhaler and the adsorbent sachet). It also cuts the continuous tube into individual packs. As a result, there is a long continuous seal 14 down the middle of the pack and the cross seals 12 at both ends.

Other package types may include more or less seals according to the desired shape of the container, which may be flat seals or crimped, and may include gussets. The seals may be formed by heating (welding) or by the use of pressure sensitive materials. In a further embodiment the flexible laminates may be formed using heat, pressure and/or vacuum into blisters or pockets to contain the product and which are then sealed by heating.

Although a flexible package is preferred, other types of enclosures or containers may be suitable, whether flexible or inflexible, provided that the enclosure chosen is impermeable, or substantially impermeable, to moisture ingress. In general, when the package or enclosure is impermeable, or substantially impermeable, to moisture, it is also impermeable, or substantially impermeable, to the propellant that gradually leaks out from the enclosed pressurized container. This may gradually build-up a pressure within the package or enclosure, which is undesirable. In this context, "substantially impermeable" to the propellant means that the level of the propellant in the enclosed volume of the package or enclosure will elevate if no measure, such as inclusion of an HFA adsorbent material, is taken to reduce it. Or in other words, the egress rate of the propellant gas allowed by the package or enclosure is lower than the rate by which it is leaked into the enclosed volume of the package or enclosure from the pressurized container. Preferably, a substantially impermeable package of the present invention has a permeability to HFA p227 that is less than or equal to about 0.25 cc of HFA p227 per square meter of package per day at about 1 bar pressure and about room temperature, or a permeability to HFA 134a that is less than or equal to about 4.1 cc of HFA 134a per square meter of package per day at about 1 bar pressure and about room temperature. Also, in this context, "impermeable" to the propellant means impenetrable by the HFA propellant gas used in the invention.

Flexible Material for Making Packages

A preferred flexible material for making the package is a laminate, although other materials may also be satisfactorily employed. The main limitations are is that the package material must be substantially impermeable to atmosphere moisture, and impermeable or substantially impermeable, to the HFS propellant used.

The laminate used in making packages generally consists of several layers of materials either co-extruded or bonded together to form an apparently single film of "laminate". As an example, a suitable laminate may have three layers adhesively laminated to each other: an inner layer, a barrier layer and an outer layer. For example, Pharmaflex Ltd., part of Alcan inc. (Cramlington, Northumberland, England) supplies a laminate film having three layers: 12 micron polyester/9 micron aluminum foil/50 micron polyethylene (product catalog LMP-F BRI/72/H1). Also, another laminate that could be used in the invention comprises polyester (16.9 gsm/12 micron, orientated and acrylic coated)/low density polyethylene (20 gsm, coloured white using Titanium dioxide)/aluminium foil (24.3 gsm/9 micron)/polyethylene copolymer (5 gsm)/low density polyethylene (13 gsm)/linear low density polyethylene (37 gsm/40 micron).

The inner layer is disposed on the inner surface of the package (i.e. the side in contact with the inhaler device) and is normally a thermoplastic layer and heat-sealable. A common material for the inner layer is polyethylene, but other polyolefinic or cyclo-olefinic materials may also be used. In addition, specialist materials such as ionomers are also frequently used for making the inner layer, for example, the ionomer under the tradename Surlyn. Properties which distinguish these ionomers resins from other polyolefin heat-sealed polymers are high clarity, high impact resistance, low haze in lamination, tear resistance, abrasion resistance, solid state toughness, and moisture imperviousness.

The barrier layer is disposed between the inner and outer layers (i.e. it is sandwiched between the inner and outer layer) and provides impermeability, or substantial impermeability, to the package. Aluminum foil is commonly used for the barrier layer, although any other metals capable of being rolled into thin sheets can also be satisfactorily used. A typical thickness for the aluminum foil layer is about 8 or 9 microns. Alternatively, the barrier layer may be metalized films, made up of tin, iron, zinc, magnesium or other metals coated by vacuum deposition or sputtering onto a polymeric sheet.

The outer layer is disposed on the surface of the barrier layer, on the opposite side to the inner layer. The outer layer normally provides support, impact resistance, protection for the barrier layer and general robustness to the pack. A commonly used material for the outer layer is polyester, although other material, such as paper, may also be used.

Adhesives may be used to join the respective layers of materials together. The adhesive layers are typically substantially smaller in thickness relative to the thickness of the substrate, heat sealable and/or protective layers which they bond.

The number, size, and shape of the layers are not limited to those layers shown in the drawings. Any number of layers with relative areas of any size and predetermined thickness may be used so long as the flexible package forms an enclosed volume which substantially prevents ingression of water vapor and particulate matter into the enclosed volume while being impermeable, or substantially impermeable to any HFA leakage from the MDI device. The size, shape, and number of layers of the package is typically a function of the size and contents of, the pressurized container which includes a drug and HFA propellant.

Preferred exemplary thicknesses of the three layers include an outer layer 1 to 40, preferably 4 to 30, more preferably 10 to 23 microns, and most preferably 12 microns; a barrier layer of 1 to 100, preferably 3 to 70, more preferably 5 to 50 microns, more preferably 6 to 20 microns and most preferably 9 microns. For the inner layer, preferred exemplary thicknesses include thicknesses of 1 to 100, preferably 5 to 70, more preferably 10 to 60, more preferably 20 to 55 microns, and most preferably 50 microns.

Preferred exemplary embodiments include a polyester film as the outer layer having a thickness ranging from 12 to 23 microns. The polyester film is laminated to an aluminum foil as the substrate layer having a thickness ranging from 6 to 20 microns. The aluminum foil is laminated to am inner film such as a polyethylene film having a thickness ranging from 20 to 50 microns.

Alternative preferred embodiments include aluminum metalized polyester film laminated to an inner layer as outlined above. Another embodiment includes a silicon oxide coplated polyester film laminated to an inner layer as outlined above. Yet, in another embodiment, a polyester film as an outer layer having a thickness ranging from 12 to 30 microns is laminated to an aluminum foil substrate layer having a thickness ranging from 6 to 20 microns, the aluminum foil being laminated to a polyester film of 12 to 30 microns which is laminated to an inner layer as outlined above. In another embodiment, a polypropylene film as an outer layer having a thickness ranging from 15 to 30 microns is laminated to an aluminum foil barrier layer having a thickness ranging from 6 to 20 microns, and the aluminum foil is laminated to an inner layer as outlined above. The laminates of the present invention can be adhesively laminated or extrusion laminated.

The laminate can be formed of any material described above and of any thickness as described above, as long as the final laminate is impermeable, or substantially impermeable, to HFA 134a or HFA p227.

The permeability, or substantial impermeability, of the laminate may be tested by a variety of techniques known to the skilled person. For example, three pieces of 75 mm diameter discs are die stamped from laminate material. The thickness of the laminate disc are then measured and recorded. The samples are then placed into test chambers and vacuumed down to 23° C. for at least three hours. Once total vacuum has stabilized approximately 50 psi of HFA p227 propellant is applied to the top half of the disc sample, this being the outlet pressure for the cylinder at laboratory temperature, whist the bottom side is still under vacuum. A similar test can be carried out using 30 psi of HFA 134a propellant applied to the top half of the disc sample.

HFA Adsorbent and Gaseous Substances "HFA adsorbent" means a substance which has the ability to condense or hold HFA molecules on its surface or in its inner structure, an activity often referred as "adsorbing" or "absorbing". Examples of HFA adsorbents material selected from the group consisting of molecular sieves, activated clays (including, montmorillonite and bentonite clay, and other known activated clays e.g. those clays supplied by Colin Stewart Minchem Ltd, Cheshire, UK), activated alumina, silica, zeolites, bauxites, and mixtures thereof. Preferably, 10 Å (Angstrom) molecular sieves.

The present invention is not limited to any specific HFA adsorbents or specific gaseous substances. Although there are many different HFA adsorbent and there are various types of propellant gases, it is believed that any propellant gas can be in principle entrapped by a properly-chosen HFA adsorbent. By following the information disclosed herein, it is well within the ordinary skill of the artisans in the field to choose a proper HFA adsorbent for a given propellant gas. Practitioners can make an initial choice based on their knowledge and experience (for example, weighing the factors such as the molecular size of the gaseous substance and the pore size of an HFA adsorbent as well as electronic charges it carries) and then conduct tests (such as those disclosed herein or some other methods) to determine the actual effectiveness of the chosen HFA adsorbent against a given propellant gas. They may need to repeat the process until a proper HFA adsorbent is found.

As described in the foregoing, applicants have found that molecular sieves with a pore size of about 10 Angstroms is an effective HFA adsorbent material. Inclusion of about 4 grams of a sachet of the molecular sieve supplied by AtoFina (Solihull, England) under the trade name Siliporite, for example, is found sufficient per package to prevent inflation. More detailed technical information about molecular sieves and their other industrial uses can be found in the Hajdu article - - - "Molecular Seives: Unique Moisture and Odor-Taste Control Material", D. Hajdu, T. J. Dangieri and S. R. Dunne, *TAPPI Polym., Laminations Coat Conf.* (1999), Vol. 2, p. 655–662, which is incorporated herein by reference.

The HFA Adsorbent Sachet

Although it is not necessary to have a sachet to contain the HFA adsorbent within the package, it is usually preferred. The HFA adsorbent sachets are commercially available from many suppliers including Sud-Chemie (Middlewich, England). The sachet, with a "tea-bag" like appearance, is generally manufactured from synthetic fibers, such as polyamide or polyester fibers or blends thereof. Commercially available materials suitable for making HFA adsorbent sachets include, for example, GDT-II from San-ei Corporation (Osaka, Japan) and Tyvek from Perfecseal (Londonderry N.lreland U.K.). However, a suitable sachet may be in other convenient shapes or appearances and made from other permeable materials. The molecular sieve material, contained within the sachet is commercially available from several manufacturers. For example AtoFina (Solihull, England) market a molecular sieve under the trade name of Siliporite.

The Pressurized Container

The pressurized container is preferably an MDI container. The term "MDI" or "metered dose inhaler" means a unit comprising a can and a drug metering device. Exemplary pressurized containers for use in MDIs are disclosed in WO 96/32151, WO 96/32345, WO 96/32150, WO 96/32099, and U.S. Pat. Nos. 6,293,279, 6,253,762, and 6,149,892.

Most often the MDI can and cap are made of aluminum or an alloy of aluminum, although other metals not affected by the drug formulation, such as stainless steel, an alloy of copper or tin plate, may be used. An MDI can may also be fabricated from glass or plastic. Preferably, however, the MDI cans employed in the present invention are made of aluminum or an alloy thereof. Advantageously, strengthened aluminum or aluminum alloy MDI cans may be employed. Such strengthened MDI cans are capable of withstanding particularly stressful coating and curing conditions, e.g., particularly high temperatures, which may be required for certain fluorocarbon polymers.

Strengthened MDI cans which have a reduced tendency to malform under high temperatures include MDI cans comprising side walls and a base of increased thickness and MDI cans comprising a substantially ellipsoidal base (which increases the angle between the side walls and the base of the can), rather than the hemispherical base of standard MDI cans. MDI cans having an ellipsoidal base offer the further advantage of facilitating the coating process.

The MDI cans of the present invention include MDI cans supplied by Presspart of Blackburn, Lancashire, U.K. , or by Neotechnic of Clitheroe, Lancashire U.K. The MDI cans typically have a neck diameter of 20 millimeters, although any suitable neck diameter may be used and can vary in height from 30 millimeters to 60 millimeters.

While there have been described and pointed out fundamental novel features of the invention as applied to a preferred embodiment thereof, it will be understood that various omissions and substitutions and changes, in the form and details of the packages and methods illustrated, may be made by those skilled in the art without departing from the spirit of the invention. For example, it is expressly intended that all combinations of those elements and/or method steps which perform substantially the same function in substantially the same way to achieve the same results are within the scope of the invention.

The invention is not limited by the embodiments described above which are presented as examples only but can be modified in various ways within the scope of protection defined by the appended patent claims.

The invention claimed is:

1. A pharmaceutical product comprising:
   (i) a pressurized MDI (metered dose inhaler) container comprising a drug, and an HFA (hydrofluoroalkane) propellant selected from the group consisting of HFA 134a and HFA p227, or a mixture thereof;
   (ii) an effective amount of an HFA adsorbent material; and
   (iii) a sealed package having an enclosed volume within which the pressurized container and the HFA adsorbent material are situated,
       wherein the sealed package is impermeable to the HFA propellant and the pressure within the enclosed volume of the package is equal to about ambient pressure; and
       wherein the HFA adsorbent material is capable of adsorbing the HFA propellant so as to maintain a constant pressure within said enclosed volume, when any leakage of the HFA propellant occurs from the pressurized container.

2. The pharmaceutical product according to claim 1, wherein the drug is selected from the group consisting of bronchodilators, antihistamines, lung surfactants, antiviral agents, corticosteroids, ant-inflammatory agents, anti-cholinergics, and antibiotics.

3. The pharmaceutical product according to claim 1, wherein the pressurized MDI (metered dose inhaler) container further comprises one or more excipients selected from the group consisting of surfactants, preservatives, flavorings, antioxidants, anti-aggregating agents and co-solvents.

4. The pharmaceutical product according to claim 1, wherein the HFA propellant is HFA 134a.

5. The pharmaceutical product according to claim 1, wherein the HFA propellant is HFA p227.

6. The pharmaceutical product according to claim 1, wherein the HFA adsorbent material is capable of adsorbing the HFA propellant up to about 25% of the weight of the adsorbent.

7. The pharmaceutical product according to claim 1, wherein the HFA gas adsorbent material is capable of adsorbing the HFA propellant up about 20% of the weight of the adsorbent.

8. The pharmaceutical product according to claim 1, wherein the HFA adsorbent material comprises material selected from the group consisting of molecular sieves, activated clays, activated alumina, silica, zeolites, bauxites, and mixtures thereof.

9. The pharmaceutical product according to claim 8, wherein the HFA adsorbent material is 10 Å (Angstrom) molecular sieves.

10. The pharmaceutical product according to claim 9, wherein the molecular sieves, in an amount of about 4 grams, absorbs about 230 ml of HFA p227.

11. The pharmaceutical product according to claim 9, wherein the molecular sieves, in an amount of about 4 grams, absorbs about 230 ml of HFA 134a.

12. The pharmaceutical product according to claim 1, wherein the package is impermeable to HFA 134a.

13. The pharmaceutical product according to claim 1, wherein the package is impermeable to HFA p227.

14. The pharmaceutical product according to claim 1, wherein the package is made of metal, glass, or plastic, and is selected from the group consisting of bottles, bags, drum boxes, and irregularly shaped containers.

15. The pharmaceutical product according to claim 14, wherein the package is made of plastic.

16. The pharmaceutical product according to claim 15, wherein the plastic is a flexible laminate having a barrier layer providing said package with impermeability to HFA 134a and/or HFA p227.

17. The pharmaceutical product according to claim 16, wherein said flexible laminate has three layers: polyester/ aluminum/polyethylene, wherein the aluminum layer is between the polyester and polyethylene layers.

18. The pharmaceutical product according to claim 16, wherein said barrier layer is. made of aluminum foil.

19. The pharmaceutical product according to claim 1, wherein the sealed package is hermetically sealed by heat-sealing, gluing, welding, brazing, mechanical closures or clamps, or compression.

20. A method for maintaining the enclosed volume of a sealed package at about ambient pressure, wherein the package contains pressurized MDI (metered dose inhaler) container comprising a drug, and an HFA (hydrofluoroalkane) propellant selected from the group consisting of HFA 134a and HFA p227, or a mixture thereof; wherein the method comprises the steps of:
  (i) positioning an effective amount of a HFA adsorbent material, and said pressurized container, within a sealable package;
  (ii) sealing the package so that the pressurized container and adsorbent are in an enclosed volume within the package at a pressure equal to about ambient pressure; and
  (iii) adsorbing any leakage of the HFA propellant into the HFA adsorbent material so as to maintain the enclosed volume at about ambient pressure;
  wherein the HFA adsorbent material is 10 Å (Angstrom) molecular sieves.

21. The method according to claim 20, wherein the molecular sieves, in an amount of about 4 grams, absorbs about 230 ml of HFA p227.

22. The method according to claim 20, wherein the molecular sieves, in an amount of about 4 grams, absorbs about 230 ml of HFA 134a.

23. A method for maintaining the enclosed volume of a sealed package at about ambient pressure, wherein the package contains pressurized MDI (metered dose inhaler) container comprising a drug, and an HFA (hydrofluoroalkane) propellant selected from the group consisting of HFA 134a and HFA p227, or a mixture thereof; wherein the method comprises the steps of:
  (i) positioning an effective amount of a HFA adsorbent material, and said pressurized container, within a sealable package;
  (ii) sealing the package so that the pressurized container and adsorbent are in an enclosed volume within the package at a pressure equal to about ambient pressure; and
  (iii) adsorbing any leakage of the HFA propellant into the HFA adsorbent material so as to maintain the enclosed volume at about ambient pressure;
  wherein the package is impermeable to HFA 134a.

24. A method for maintaining the enclosed volume of a sealed package at about ambient pressure, wherein the package contains pressurized MDI (metered dose inhaler) container comprising a drug, and an HFA (hydrofluoroalkane) propellant selected from the group consisting of HFA 134a and HFA p227, or a mixture thereof; wherein the method comprises the steps of:
  (i) positioning an effective amount of a HFA adsorbent material, and said pressurized container, within a sealable package;
  (ii) sealing the package so that the pressurized container and adsorbent are in an enclosed volume within the package at a pressure equal to about ambient pressure; and
  (iii) adsorbing any leakage of the HFA propellant into the HFA adsorbent material so as to maintain the enclosed volume at about ambient pressure;
  wherein the package is impermeable to HFA p227.

25. A method for maintaining the enclosed volume of a sealed package at about ambient pressure, wherein the package contains pressurized MDI (metered dose inhaler) container comprising a drug, and an HFA (hydrofluoroalkane) propellant selected from the group consisting of HFA 134a and HFA p227, or a mixture thereof; wherein the method comprises the steps of:
  (i) positioning an effective amount of a HFA adsorbent material, and said pressurized container, within a sealable package;
  (ii) sealing the package so that the pressurized container and adsorbent are in an enclosed volume within the package at a pressure equal to about ambient pressure; and
  (iii) adsorbing any leakage of the HFA propellant into the HFA adsorbent material so as to maintain the enclosed volume at about ambient pressure; wherein the package is made of plastic and wherein the plastic is a flexible laminate having a barrier layer providing said package with impermeability to HFA 134a and/or HFA p227.

26. The method according to claim 25, wherein said flexible laminate has three layers: polyester/aluminum/polyethylene, wherein the aluminum layer is between the polyester and polyethylene layers.

27. The method according to claim 25, wherein said barrier layer is made of aluminum foil.

28. A pharmaceutical product comprising:
  (i) pressurized MDI (metered dose inhaler) container comprising a drug, and an HFA (hydrofluoroalkane) propellant selected from the group consisting of HFA 134a and HFA p227, or a mixture thereof;
  (ii) an effective amount of an HFA adsorbent material; and
  (iii) a sealed package having an enclosed volume within which the pressurized container and the HFA adsorbent material are situated,
  wherein the pressure within the enclosed volume of the package is equal to about ambient pressure;
  wherein the HFA adsorbent material is capable of adsorbing the HFA propellant so as to maintain a constant pressure within said enclosed volume, when any leakage of the HFA propellant occurs from the pressurized container; and
  wherein the package has a permeability to HFA p227 that is less than or equal to about 0.25 cc of HFA p227 per square meter of package per day at about 1 bar pressure and about room temperature, or a permeability to HFA 134a that is less than or equal to about 4.1 cc of HFA 134a per square meter of package per day at about 1 bar pressure and about room temperature; wherein
  the HFA adsorbent material is 10 Å molecular sieves.

29. A pharmaceutical product according to claim 28, wherein the molecular sieves, in an amount of about 4 grams, absorbs about 230 ml of HFA p227.

30. A phannaceutical product according to claim 28, wherein the molecular sieves, in an amount of about 4 grams, absorbs about 230 ml of HFA 134a.

* * * * *

UNITED STATES PATENT AND TRADEMARK OFFICE
CERTIFICATE OF CORRECTION

PATENT NO. : 7,025,205 B2
APPLICATION NO. : 10/603214
DATED : April 11, 2006
INVENTOR(S) : Barker It is certified that error appears in the above-identified patent and that said Letters Patent is hereby corrected as shown below:

Column 21,
Line 4, "wherein said barrier layer is. made of aluminum foil." should read
-- wherein said barrier layer is made of aluminum foil. --.

Column 22,
Line 33, "(i) pressurized MDI (metered dosc inhaler) container" should read
-- (i) a pressurized MDI (metered dose inhaler) container --.
Line 61, "30. A phannaccutical product according to claim 28," should read
-- 30. A pharmaceutical product according to claim 28, --.

Signed and Sealed this

Twentieth Day of June, 2006

JON W. DUDAS
*Director of the United States Patent and Trademark Office*